US008461561B2

(12) United States Patent
Freeman et al.

(10) Patent No.: US 8,461,561 B2
(45) Date of Patent: *Jun. 11, 2013

(54) SYSTEM FOR RADIATION STERILIZATION OF MEDICAL DEVICES USING A PACKAGE HAVING MODIFIER SECTIONS

(75) Inventors: Abigail Freeman, Fremont, CA (US); Gregory S. Simmons, Temecula, CA (US); Brian D. Riggs, Temecula, CA (US); Robert Harrison, Perris, CA (US); Dan Castro, Santa Clara, CA (US); Bin Huang, Pleasanton, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/240,804

(22) Filed: Sep. 22, 2011

(65) Prior Publication Data
US 2012/0007003 A1 Jan. 12, 2012

Related U.S. Application Data

(62) Division of application No. 11/803,829, filed on May 15, 2007, now Pat. No. 8,034,287.

(60) Provisional application No. 60/810,300, filed on Jun. 1, 2006.

(51) Int. Cl.
*H01J 5/18* (2006.01)
*A61L 2/00* (2006.01)

(52) U.S. Cl.
USPC ............................. 250/505.1; 422/22

(58) Field of Classification Search
USPC ................................. 422/22; 250/505.1
See application file for complete search history.

(56) References Cited

U.S. PATENT DOCUMENTS

| 5,825,042 | A | 10/1998 | Strobel et al. |
| 6,594,156 | B1 | 7/2003 | Van Antwerp et al. |
| 7,694,813 | B2 * | 4/2010 | Shalaby ............... 206/438 |
| 7,964,136 | B2 * | 6/2011 | Sabaria ............... 422/22 |
| 8,034,287 | B2 | 10/2011 | Freeman et al. |
| 2004/0267347 | A1 * | 12/2004 | Cervantes ........... 623/1.11 |
| 2007/0065334 | A1 | 3/2007 | Shalaby |
| 2008/0286144 | A1 * | 11/2008 | Shalaby ............... 422/22 |
| 2010/0323093 | A1 | 12/2010 | Chen et al. |

FOREIGN PATENT DOCUMENTS

| EP | 0 218 003 | 4/1987 |
| EP | 1 518 563 | 3/2005 |
| JP | 08-275991 | 10/1996 |
| JP | 11 133196 | 5/1999 |
| JP | 2000 334028 | 12/2000 |
| JP | 2002-078780 | 3/2002 |
| JP | 2005-249671 | 9/2005 |
| WO | WO 03/037390 | 5/2003 |
| WO | WO 2006/034157 | 3/2006 |

OTHER PUBLICATIONS

Translated Notice of Reasons for Rejection from JPO, mailed Feb. 2, 2012, 4 pgs.
International Search Report for PCT/US2007/0129930 filed Jun. 1, 2007, mailed Dec. 18, 2007, 5 pgs.
European Search Report for EP11195791 mailed Mar. 2, 2012, 6 pgs.

* cited by examiner

*Primary Examiner* — Regina M Yoo
(74) *Attorney, Agent, or Firm* — Squire Sanders (US) LLP

(57) ABSTRACT

Methods and systems for selection radiation exposure in sterilization of medical devices are disclosed.

17 Claims, 8 Drawing Sheets

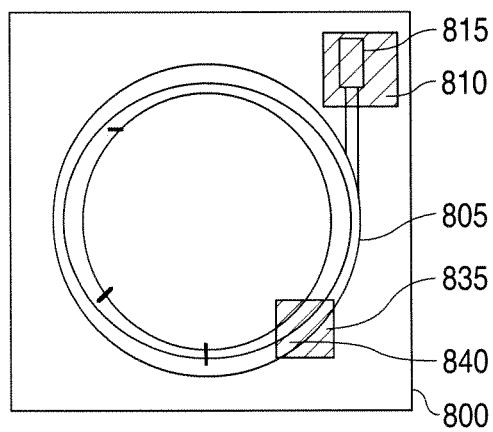 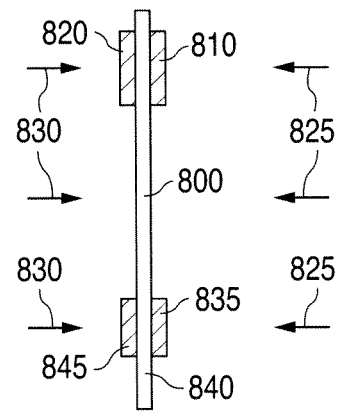
FIG. 8A  FIG. 8B
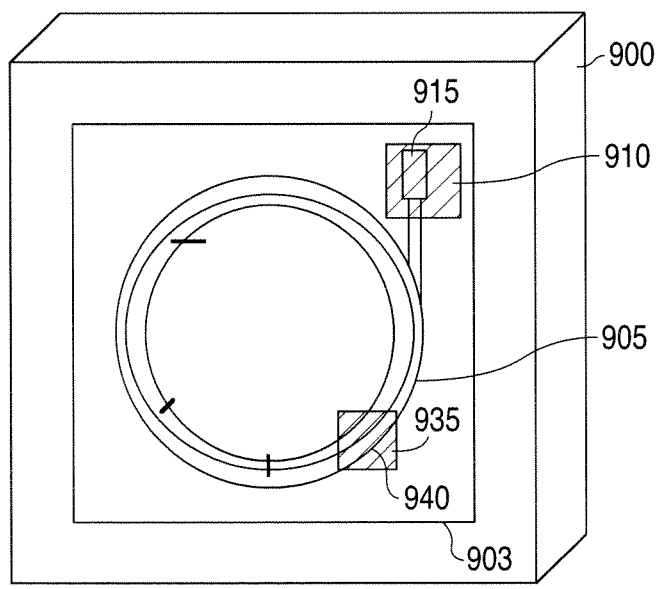 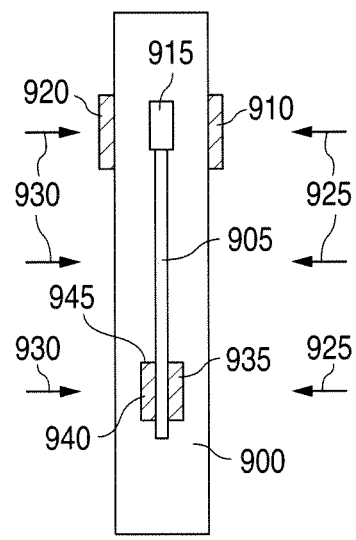
FIG. 9A  FIG. 9B

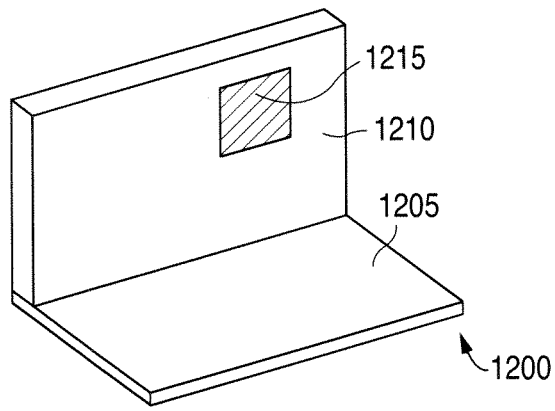 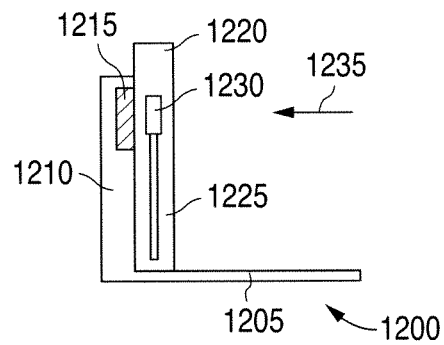
FIG. 12A  FIG. 12B
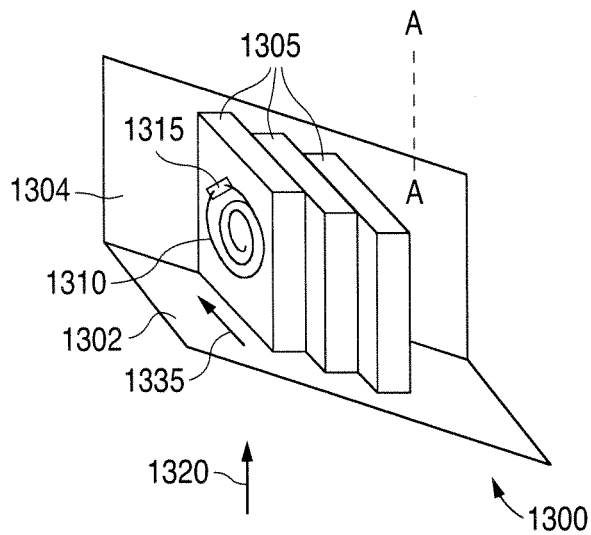
FIG. 13A
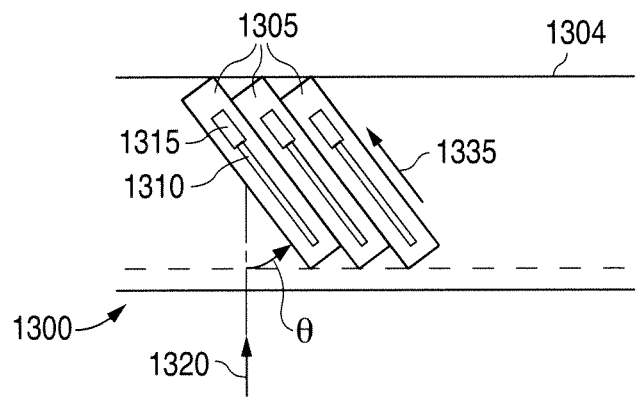
FIG. 13B

SYSTEM FOR RADIATION STERILIZATION OF MEDICAL DEVICES USING A PACKAGE HAVING MODIFIER SECTIONS

CROSS-REFERENCE TO RELATED APPLICATION

This is a divisional of U.S. application Ser. No. 11/803,829 filed May 15, 2007 which claims priority to U.S. provisional application No. 60/810,300 filed Jun 1, 2006.

BACKGROUND OF THE INVENTION

1. Field of the Invention

This invention relates to radiation sterilization.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

After a stent is fabricated, a stent typically undergoes sterilization to reduce the bioburden of the stent to an acceptable sterility assurance level (SAL). There are numerous methods of sterilizing medical devices such as stents, the most common being ethylene oxide treatment and treatment with ionization radiation such as electron beam and gamma radiation. Generally, it is desirable for the sterilization procedure to have little or no adverse affects on the material properties of the stent.

SUMMARY

Various embodiments of the present invention include a method of sterilizing a stent delivery assembly comprising: exposing a stent delivery assembly to radiation from a radiation source, wherein a covering over a selected section of the assembly selectively modifies the radiation from the radiation source that is delivered to the selected section of the assembly.

Further embodiments of the present invention include a method of sterilizing a stent delivery assembly comprising: exposing a stent delivery assembly enclosed in a package to radiation from a radiation source, wherein the package comprises one or more modifier sections, the modifier sections selectively modify the radiation from the radiation source that is delivered to the selected section of the assembly.

Additional embodiments of the present invention include a system for sterilizing a stent delivery assembly with radiation, comprising: a stent delivery assembly; and a package having a one or more modifier sections, the assembly being disposed within the package, wherein the one or more modifier sections are positioned relative to a selected section of the assembly to modify radiation delivered to the selected section of the assembly when radiation is directed at the assembly from a radiation source.

Other embodiments of the present invention include a system for sterilizing a stent delivery assembly with radiation, comprising: a stent delivery assembly; and a covering over a selected section of the assembly, wherein the covering modifies radiation delivered to the selected section of the assembly when radiation is directed at the assembly from a radiation source.

Certain additional embodiments of the present invention include a method of sterilizing a stent delivery assembly comprising: exposing a stent delivery assembly to radiation from a radiation source, the assembly being disposed in a package supported by a fixture, wherein a modifier section of the fixture selectively modifies the radiation from the radiation source that is delivered to a selected section of the assembly.

Some other embodiments of the present invention include a method of sterilizing a plurality of stent delivery system assemblies with a radiation source, the method comprising: positioning a plurality of stent catheter assemblies within packages supported on a fixture, each of the assemblies arranged in a planar configuration in the packages; and exposing the assemblies to a radiation beam from a radiation source, the beam being at an acute angle to the planar configuration of the packages that are positioned between the source and the fixture, wherein the packages are arranged such that the radiation passes through more than one of the assemblies during exposure, the delivered dose varying with distance between the radiation source and the fixture, one or more of the assemblies being positioned within the packages so that a selected section of the assemblies receives a selected delivered radiation dose.

BRIEF DESCRIPTION OF THE DRAWINGS

FIG. 8A depicts a schematic illustration of a flexible package with a stent delivery assembly contained therein.

FIG. 8B depicts a side view of the package of FIG. 8A.

FIG. 9A depicts a schematic illustration of a rigid package with a stent delivery assembly contained therein.

FIG. 9B depicts a side view of the package of FIG. 9A.

FIG. 12A depicts a fixture for supporting packages containing stent delivery assemblies during sterilization.

FIG. 12B depicts a side view of the fixture of FIG. 11B supporting a package containing a stent delivery assembly.

FIG. 13A depicts a fixture containing packages arranged in a staggered horizontally stacked configuration.

FIG. 13B depicts an overhead view of the fixture in FIG. 13A.

DETAILED DESCRIPTION OF THE INVENTION

Various embodiments of the present invention relate to sterilizing implantable medical devices with radiation. In some embodiments, the devices can be made in whole or in part of polymers. The embodiments relate to controlling the radiation delivered to selected sections of a device.

The method and systems described herein may be applied generally to implantable medical devices. The methods and systems are particularly relevant, for reasons discussed below, to implantable medical devices having a polymeric substrate, a polymer-based coating, and/or a drug-delivery coating. A polymer-based coating may contain, for example, an active agent or drug for local administration at a diseased site. An implantable medical device may include a polymer or non-polymer substrate with a polymer-based coating.

Examples of implantable medical devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Abbott Cardiovascular Systems Inc, Santa Clara, Calif.). The underlying structure or substrate of the device can be of virtually any design.

Figure 1:
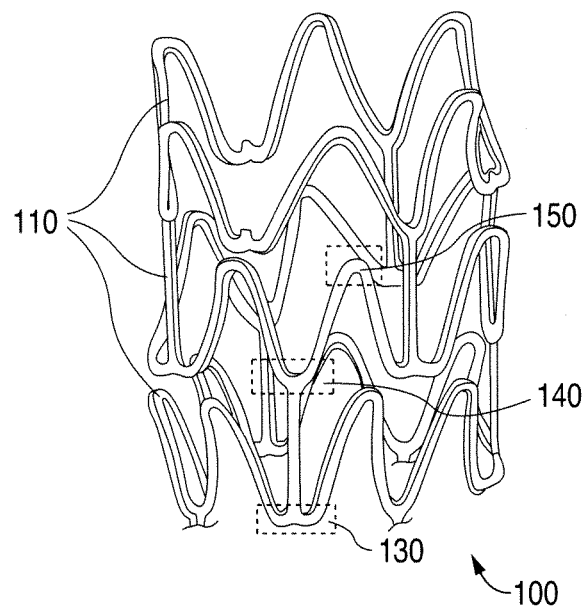
FIG. 1 depicts a stent.

The structure of a stent in particular can have a scaffolding or a substrate that includes a pattern of a plurality of interconnecting structural elements or struts. FIG. 1 depicts an example of a view of a stent 100. Stent 100 has a cylindrical shape and includes a pattern with a number of interconnecting structural elements or struts 110. In general, a stent pattern is designed so that the stent can be radially compressed (crimped) and radially expanded (to allow deployment). The stresses involved during compression and expansion are generally distributed throughout various structural elements of the stent pattern. The present invention is not limited to the stent pattern depicted in FIG. 1. The variation in stent patterns is virtually unlimited.

A stent such as stent 100 may be fabricated from a polymeric tube or a sheet by rolling and bonding the sheet to form a tube. A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

A stent has certain mechanical requirements that are crucial to successful treatment. For example, a stent must have sufficient radial strength to withstand structural loads, namely radial compressive forces, imposed on the stent as it supports the walls of a vessel. In addition, the stent must possess sufficient flexibility to allow for crimping, expansion, and cyclic loading. Bending elements 130, 140, and 150, in particular, are subjected to a great deal of stress and strain during use of a stent.

It is well known by those skilled in the art that the mechanical properties of a polymer can be modified by applying stress to a polymer. The strength and modulus of a polymer tend to be increased along the direction of the applied stress. Therefore, in some embodiments, a polymer tube can be radially deformed prior to laser cutting to enhance radial strength. The increase in strength and modulus can be due to the induced molecular orientation in the circumferential direction. However, as the temperature of the polymer increases close to or above a glass transition temperature (Tg), some or all of the induced orientation and strength can be lost due to relaxation of polymer chains. The "glass transition temperature," Tg is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

Sterilization is typically performed on medical devices, such as stents, to reduce the bioburden on the device. Bioburden refers generally to the number of microorganisms with which an object is contaminated. The degree of sterilization is typically measured by a sterility assurance level (SAL) which refers to the probability of a viable microorganism being present on a product unit after sterilization. The required SAL for a product is dependent on the intended use of the product. For example, a product to be used in the body's fluid path is considered a Class III device. SAL's for various medical devices can be found in materials from the Association for the Advancement of Medical Instrumentation (AAMI) in Arlington, Va.

Radiation sterilization is well known to those of ordinary skill the art. Medical devices composed in whole or in part of polymers can be sterilized by various kinds of radiation, including, but not limited to, electron beam (e-beam), gamma ray, ultraviolet, infra-red, ion beam, x-ray, and laser sterilization. A sterilization dose can be determined by selecting a dose that provides a required SAL. A sample can be exposed to the required dose in one or multiple passes.

However, it is known that radiation can alter the properties of the polymers being treated by the radiation. High-energy radiation tends to produce ionization and excitation in polymer molecules. These energy-rich species undergo dissociation, subtraction, and addition reactions in a sequence leading to chemical stability. The stabilization process can occur during, immediately after, or even days, weeks, or months after irradiation which often results in physical and chemical cross-linking or chain scission. Resultant physical changes can include embrittlement, discoloration, odor generation, stiffening, and softening, among others.

In particular, the deterioration of the performance of polymeric materials and drugs due to e-beam radiation sterilization has been associated with free radical formation in a device during radiation exposure and by reaction with other parts of the polymer chains. The reaction is dependent on e-beam dose and level of temperature.

Additionally, exposure to radiation, such as e-beam can cause a rise in temperature of an irradiated polymer sample. The rise in temperature is dependent on the level of exposure. It has been observed that a stent delivery assembly can increase about 7° C. per 12 kGy of radiation exposure. Mechanical properties of polymers are particularly sensitive to changes in temperature. In particular, the effect on properties becomes more profound as the temperature approaches and surpasses the glass transition temperature, Tg. It has been observed that e-beam radiation of polymer stents can result in cracking of struts during deployment due to onset of brittle behavior. The cracking can be due to the increase in temperature, as well as the reduction in molecular weight. Additionally, the increase in temperature can result in a loss of some or all of the induced orientation and strength due to relaxation of polymer chains.

Furthermore, the increase in temperature can also increase the release rate of drug resulting in a decrease of drug loading on a stent. Drugs can also degrade at increased temperatures during manufacture and storage conditions, altering the total content and release rate of the drug. The dose can be selected to be sufficient to sterilize the stent to a desired degree. As indicated above, the exposure can be in one or more passes from a radiation source.

In general, a polymeric stent and balloon are more sensitive to radiation exposure than a catheter and dispenser coil. The performance of the stent and balloon are more likely to be adversely affected by the increase in temperature and chemical degradation caused by radiation exposure. Therefore, it is important for the delivered radiation exposure to the stent and balloon to be within a selected range. A selected range can be, for example, 20-30 KGy or, more narrowly, 22-27 KGy. On the other hand, the performance of a catheter and dispenser coil is less sensitive to radiation exposure. Thus, the catheter and dispenser coil can tolerate larger variations in delivered radiation at higher levels. In general, selected sections of a device can have different desired or optimal delivered radiation range than other sections of the device.

Furthermore, in some embodiments, the stent and balloon may require a lower radiation exposure for effective sterilization than the catheter and dispenser coil. The processing of a stent may result in a lower level of bioburden on the stent compared to the catheter. For example, a stent may be exposed to solvents such as isopropyl alcohol and acetone during processing. Additionally, stent material may be exposed to high temperatures during various processing steps. Thus, the stent can have a bioburden less than 5 cfu and even as low as 0-1 cfu. "CFU" is a measure of bioburden that stands for "colony-forming unit" which is a measure of viable bacterial numbers. The required or terminal sterilization dose for a product with 1.5 cfu is 15 KGy and a radiation dose for an 8 cfu product is 17.5 KGy. The delivery system may require substantially higher doses than other parts of the assembly.

Therefore, for a given dose of radiation from a radiation source, it may be desirable to selectively modify the radiation delivered to a selected section of an implantable medical device such as a stent delivery assembly. For example, the delivered dose to a stent can be decreased. This would reduce the degradation of the performance due to radiation. Alternatively, it may be desirable to increase a delivered dose to a selected section of a device. Some sections of the device may require a higher dose due to high bioburden. Also, some sections may receive a lower delivered dose than required due to shielding of radiation from packaging or other portions of the device.

Figure 2:
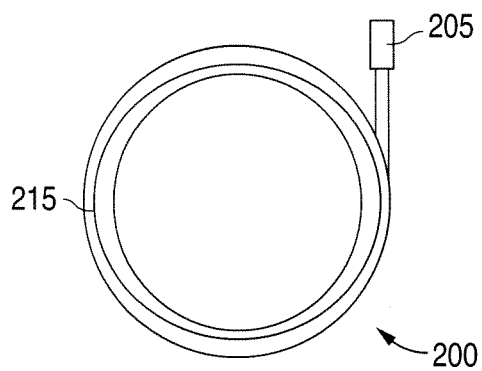
FIG. 2 depicts a stent delivery assembly.

Stents are typically sterilized, packaged, stored, and transported in a "ready to implant" configuration in which the stent is disposed at the distal end of a delivery system that includes a catheter and dispenser coil. FIG. 2 depicts a stent delivery assembly 200 with a stent 205 disposed on a distal end of a delivery system 215. Stent 205 can be crimped over a balloon. A sheath can also be disposed over the stent to secure the secure to the balloon. Stent delivery assembly 200 can be packaged prior to or after radiation sterilization.

Figure 3:
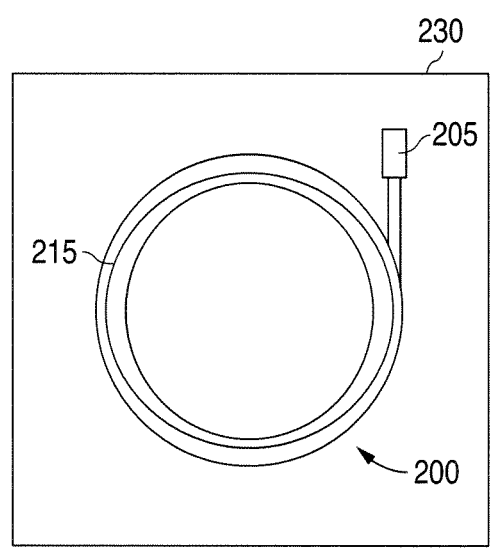
FIG. 3 depicts a schematic illustration of a stent delivery assembly disposed in a pouch.

Stents and stent delivery assemblies are typically stored, transported, as well as sterilized in sealed storage containers. Such containers are adapted to protect the assembly from damage and environmental exposure (humidity, oxygen, light, etc.) which can have an adverse effect on the stent. Storage containers for a stent and delivery system can be designed to be any convenient form or shape that permits the effective enclosure of a stent and delivery system assembly contained therein. The container, however, may be compact and shaped so as to minimize storage space occupied by the container. A container intended primarily to protect the stent and delivery system from environmental exposure can be a pouch or sleeve. FIG. 3 depicts a schematic illustration of stent delivery assembly 200 disposed in a pouch 230. As can be seen from FIG. 3, assembly 200 is disposed or stored in a planar configuration.

In one commercially useful embodiment, a pouch can have a rectangular cross-section with a width between 8 in and 12 in and a length between 10 in and 13 in. Also, depending on the types of substance(s) used to construct the pouch, the container can be of various degrees of rigidity or flexibility. The container can be constructed of flexible films rather than rigid materials because it is less likely that the seal would be compromised by a change in atmospheric conditions during storage. For example, the container can be constructed of two sheets or lamina which have been joined along an edge. Also, the container can be constructed of a single sheet or lamina which has been folded and sealed along all edges or along all non-folded edges; or a bag or pocket which is sealed along one or more edges. The pouches can be made from a polymer, glass, ceramic, metallic substance, or a combination thereof. Typically, the pouches are made of metallic foil.

Figure 4A:
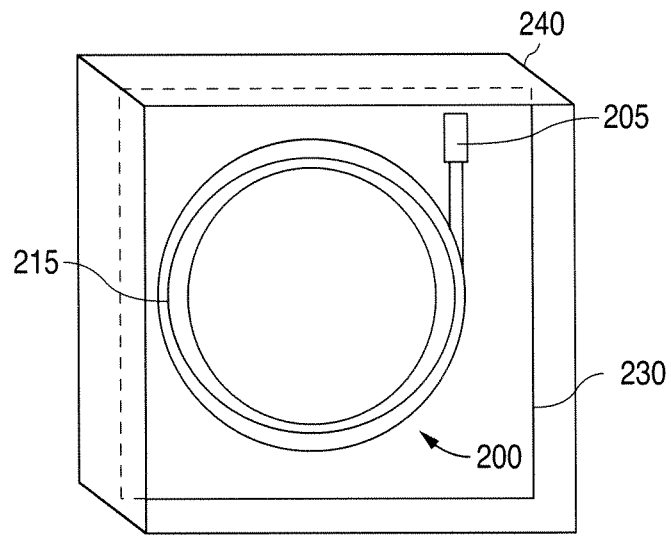
FIG. 4A depicts a schematic illustration of a stent delivery assembly in a pouch disposed in a flat box.
Figure 4B:
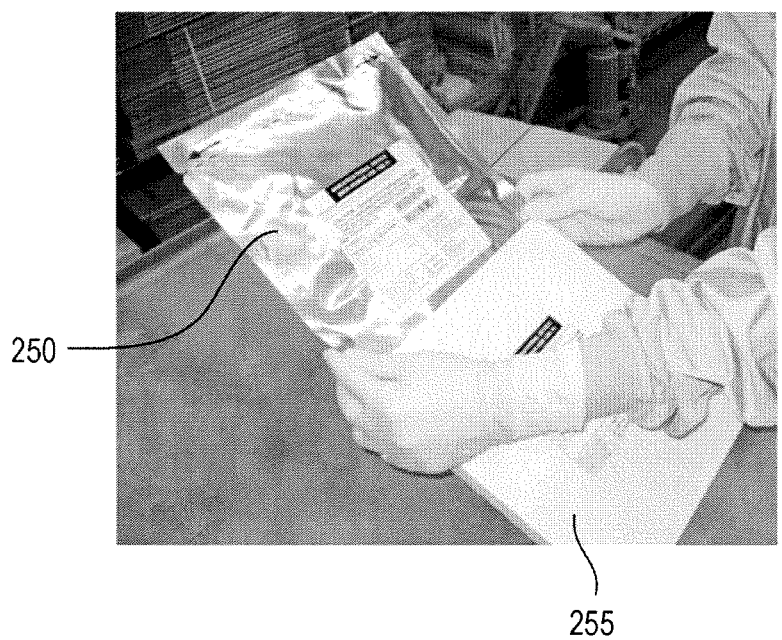
FIG. 4B depicts a photograph of a pouch containing a stent delivery assembly being disposed in a chipboard box.

A pouch containing a stent and delivery system can be further disposed within a rigid container to protect the pouch and the stent and delivery system contained therein. The rigid container can be, for example, a box, such as a chipboard box. FIG. 4A depicts a schematic illustration of a stent and delivery system 200 within pouch 230 in a flat chipboard box 240. FIG. 4B depicts a photograph of a pouch 250 containing a stent and delivery system being disposed in a chipboard box 255.

Figure 5:
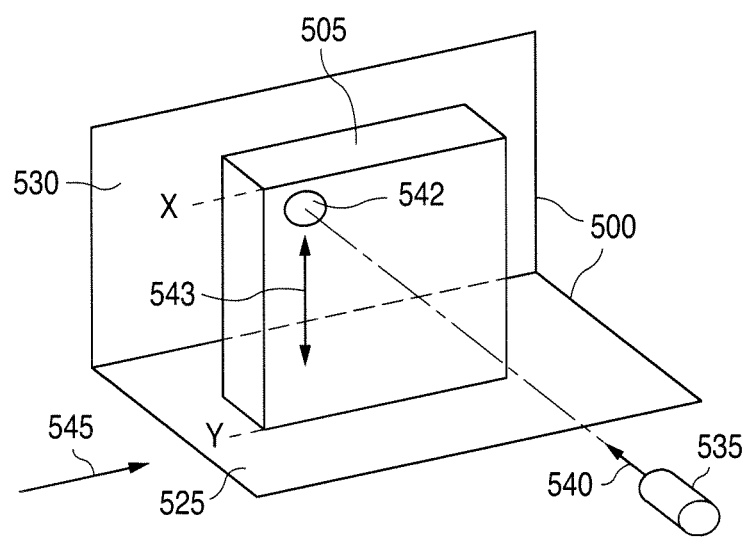
FIG. 5 depicts a schematic illustration of a fixture that supports a package.

A system for sterilizing a packaged stent delivery assembly includes a radiation source, such as an e-beam source, and a fixture for supporting the package. The support fixture is moved, for example, on a conveyer arrangement past an e-beam source in a manner that an e-beam is directed onto the stent delivery assembly. FIG. 5 depicts a schematic illustration of a fixture 500 that supports a package 505 containing a stent delivery assembly (not shown). Fixture 500 includes a bottom support 525 and a back support arm 530. A radiation source 535 directs radiation, as shown by an arrow 540. Fixture 500 can be moved by a conveyer system (not shown) as shown by an arrow 545 past radiation source 535 to sterilize the stent delivery assembly in package 505.

In some embodiments, the cross-section of an E-beam is circular or generally circular in shape, as depicted by a pulse 542 of an E-beam. In such embodiments, the E-beam is pulsed up and down as shown by an arrow 543 to irradiate package 505 and the stent delivery assembly along an axis from position X to position Y. Thus, as fixture 500 is conveyed in the direction shown by arrow 545, an entire selected portion of package 505 and stent delivery assembly can be irradiated. In such embodiments, the beam can pulse up and down, for example, 64 times a second.

As indicated above, the radiation delivered by a radiation source to selected sections of an implantable medical device, as shown in FIG. 5, may be greater or smaller than desired. In certain embodiments of the present invention, a covering over a selected section of an implantable medical device, such as a stent delivery assembly, selectively modifies the radiation from the radiation source that is delivered to the selected section of the assembly. In one embodiment, the radiation can be modified by the covering so that radiation delivered to the selected section is within an optimal delivered radiation range. The covering can selectively modify radiation from a radiation source so that radiation delivered to a selected section of the assembly is higher or lower than the radiation delivered to the selected section without the covering.

In other embodiments, an implantable medical device can be enclosed in a package including one or more modifier sections. The modifier sections can selectively modify the radiation from the radiation source that is delivered to the selected section of the assembly In one embodiment, the radiation can be modified by the modifier sections(s) so that radiation delivered to the selected section is within an optimal delivered radiation range. The modifier sections can selectively modify radiation from a radiation source so that radiation delivered to a selected section of the assembly is higher or lower than the radiation delivered to the selected section in the absence of the modifier sections.

As indicated above, radiation barriers, such as a covering and the modifier sections, can increase or decrease the radiation delivered to the selected section. Radiation barriers can cause such increase/decrease through absorption, reflection (or backscattering), or a combination of thereof. The manner of modification of radiation depends upon factors such as the thickness, density, and the reflective properties of a covering or modifier section material.

Figure 6A:
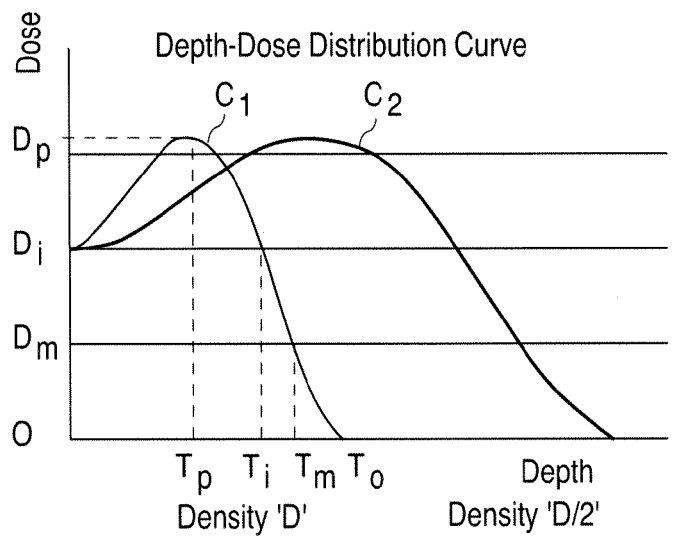
FIG. 6A depicts the delivered dose within a material versus the depth of penetration of the radiation for materials of two different densities.

Generally, the delivered dose within a material that absorbs radiation varies with both the depth of penetration (thickness) and the density of a material. FIG. 6A depicts the delivered dose within a radiation absorbing material versus the depth of penetration of the radiation for materials of two different densities, curves C1 and C2.

FIG. 6A shows that, depending on its thickness, a radiation barrier element can increase or decrease delivered radiation or dose above or below the initial radiation, Di. FIG. 6A shows dose versus the density (or depth) the electrons traveled through. Di could be the radiation dose that a selected section would receive in the absence of a barrier between the selected section and radiation source or backscattering from material on a side opposite the selected section from the radiation source. FIG. 6A also shows that the range of increased radiation increases to larger thicknesses as the density of the radiation barrier element increases. Both the density and thickness of a barrier element material can be selected to obtain selected radiation delivered on a selected section. When sterilizing multiple devices sequentially or simultaneously, in order for all of the device to receive an equal amount of dose in a selected section (e.g., all the stents the same dose) the electrons must travel through equal density by the time it hits the selected section. Various materials are known by those of skill in the art that absorb or modify radiation including various types and forms of polymers, such as foam. "Foam" can refer to a polymer foam, for example, polystyrene foam such as Styrofoam from Dow Chemical Company, Midland, Mich.

A radiation barrier can modify or reduce radiation by reflecting or backscattering radiation. In addition to a radiation barrier such as a covering or modifier sections of a package, radiation from the radiation source can be backscattered to a device from, for example, from a part of a supporting fixture back (e.g., support arm 530 in FIG. 5). Metals, generally, have a tendency to reflect various kinds of radiation, such as, electromagnetic radiation, electron beam, and ion beam radiation. Representative metals that may be used to as a reflective barrier material include aluminum and stainless steel.

Packaging, fixture, barriers, etc., can be designed so the radiation does not go through enough density to drop the dose to the selected section to zero. Additionally, the packaging, fixture, barriers, etc., can be designed so that a selected section receives a minimum dose, Dm, for example, 25 kGy. Curve C1 rises from Di to Dp and then goes down to Dm, and finally to zero. Thus, there is a large dose variation.

Embodiments of the present invention include selective modification of radiation to obtain a selected delivered radiation dose at a selected section of a device. As described below, selective modification of radiation can be performed using a covering, modifier section(s) in packaging, a fixture, or a combination thereof. Three sets of embodiments of selective modification are described herein.

In a first set of embodiments, the radiation can be selectively modified with a barrier between the radiation source and the selected section. The barrier is in front of the selected section, so that the radiation from the radiation source passes through the barrier to the selected section. In such embodiments, the thickness, density of material, or both of the barrier can be selected to obtain a selected radiation dose to the selected section.

In a second set of embodiments, a barrier in back of or on a side of the selected section opposite the incoming radiation selectively modifies radiation. In one such embodiment, the radiation can be selectively modified with a barrier made from reflective material that backscatters or reflects radiation back to the selected section. The radiation passes through the selected section to the barrier which reflects a portion of the radiation back at the selected section. The total dose delivered to the selected section is a sum of the radiation that initially passes through the selected section and the reflected radiation.

In an alternative embodiment of the second set of embodiments, the barrier is made from a non-reflective material. The barrier can act as a barrier that reduces or prevents radiation backscattered from, for example, a part of a fixture from increasing the radiation delivered to the selected section.

In a third set of embodiments, the radiation can be selectively modified with a barrier in front of and behind the selected section. Radiation passes through the front barrier to the selected section and then is backscattered to the selected section by the back barrier. The total dose delivered to the selected section is a sum of the radiation modified by the first barrier and radiation reflected from the back barrier to the selected section. In such embodiments, the properties of the front barrier (thickness, density) and the reflective properties of the back barrier can be selected to obtain a selected delivered radiation dose to the selected section.

Figure 6B:
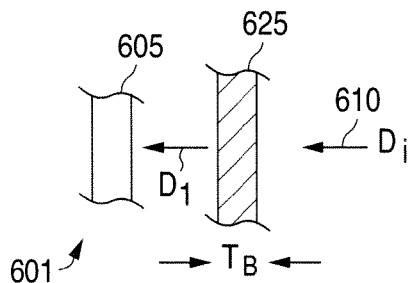
FIGS. 6B-D depict embodiments of modifying radiation exposure to a selection section of device.
Figure 6C:
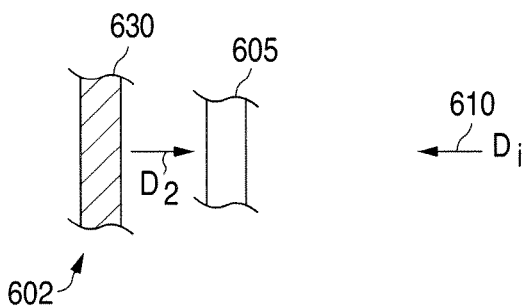
Figure 6D:
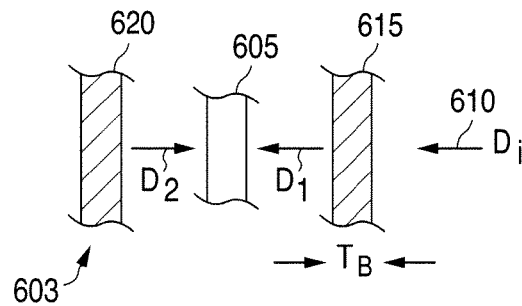

FIGS. 6B-D illustrate the first set, second set, and third set of embodiments, respectively. FIGS. 6B-D depict close-up views of a cross-section of a selected section 605 of an implantable medical device with radiation Di directed at the device as shown by an arrow 610.

FIG. 6B, which illustrates the first set of embodiments, depicts a configuration 601 with a radiation barrier 625. In FIG. 6B, radiation barrier 625 can correspond to a part of a covering or modifier section of a package on a side of selected section 605 facing incoming radiation 610 with dose, Di. Radiation 610 can be modified by barrier 625 to have dose D1, which is the radiation delivered to selected section 605.

In FIG. 6B, the radiation delivered to the selected section can be increased above Di or decreased below Di. Barrier 625 can be a material with a dose curve C1 from FIG. 6A. D1 can be increased to be above Di if the thickness of barrier 605 is less than Ti, as shown in FIG. 6A. D1 can be decreased to be below Di if the thickness is greater than Ti. To obtain a selected delivered dose with a thinner barrier, a higher density material can be used. In an increases D1 to 44 kGy. The thickness, for example, can be changed so that D1 is decreased to 30 kGy. An exemplary embodiment of a barrier material can be a metal.

FIG. 6C, which illustrates the second set of embodiments, depicts a configuration 602 with a radiation barrier 630 behind selected section 605. The radiation delivered to the selected section can be increased above Di. Radiation barrier 630 can correspond to a part of a covering, modifier section, or fixture on a side of selected section 605. Even if barrier 630 is a non-reflective material, an increase in delivered radiation due to reflection of radiation to selected section 605 from a side opposite to selected section 605 is reduced or prevented. If barrier 630 is a reflective material, a portion, D2, of radiation 610 is reflected at selected section 605. The total delivered radiation is the sum of Di and D2.

In an exemplary embodiment, Di is 25 kGy so that the initial exposure is 25 kGy. A portion, D2, of the 25 kGy radiation is reflected by barrier 630, for example, 5 kGy. The total delivered radiation is the sum of Di and D2, or 30 kGy.

FIG. 6D, which illustrates the third set of embodiments, depicts a barrier 615 in front of selected section 605 and a barrier 620 behind selected section 605. Radiation 610 can be modified by barrier 615 to have dose D1. D1 can be higher or lower than Di, depending on the thickness and density of barrier 615.

If barrier 620 is a reflective material, a portion of radiation 610, D2, is reflected back at selected section 605. The total delivered radiation is the sum of D1 and D2. There are at least three possibilities with a barrier 620 being a reflective material:

(1) The total delivered radiation is above Di if barrier 615 has a thickness and density such that D1 is greater than Di and D2 further increases the total above Di (2) The total delivered radiation is above Di if barrier 615 has a thickness and density such that D1 is less than Di and D2 increases the total above Di.

(3) The total delivered radiation to selected section 605 is below Di if barrier 615 has a thickness and density such that D1 is less than Di and the sum of D1 and D2 is less than Di.

If barrier 620 is a non-reflective material, the total delivered radiation can be higher or lower than Di, depending on the thickness and density of barrier 615.

In an exemplary embodiment, barrier 620 is a reflective material and Di is 40, D1 is 44 kGy, and D2 is 6 kGy. The total delivered dose is 50 kGy.

In some embodiments, a covering can include a sheath or a sleeve that is disposed around a selected section of a stent delivery assembly. In such embodiments, the selected section can include a stent with the sheath or sleeve disposed around the circumference of the stent. Additionally, the selected section can be strip of polymeric material folded over to enclose a selected section of the assembly and clipped to secure the folded over strip.

In some embodiments, the covering for the selected section includes a first side and a second side. The first side covers a side of the selected section facing incoming radiation and the second side covers a side of the selected section opposite the incoming radiation. The first side can modify the radiation through absorption. The second side can modify the radiation by backscattering of radiation at the selected section. Alternatively, the covering is composed of a non-reflective material so that there is little modification through backscattering. In another embodiment, the covering covers a side of the selected section facing incoming radiation with a side of the selected section opposite the incoming radiation being free of the covering.

Figure 7A:
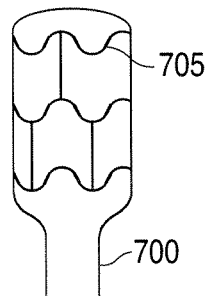
FIG. 7A depicts a stent disposed over a distal end of a catheter.
Figure 7B:
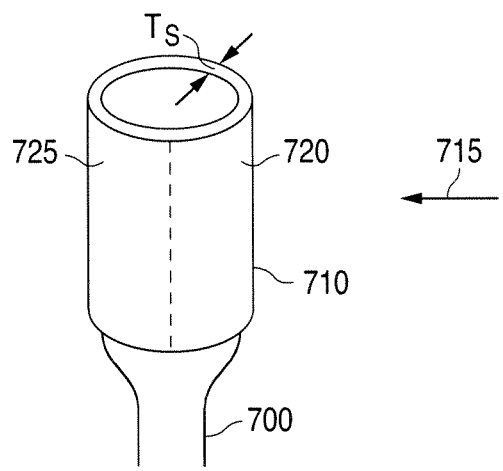
FIG. 7B depicts a sheath disposed over stent.

FIG. 7A depicts a stent 705 disposed over a distal end 700 of a catheter. FIG. 7B depicts a sheath 710 disposed over stent 705. Sheath 710 can also be closed at a distal end to reduce or prevent exposure of the stent to bioburden. Sheath 710 can serve the dual purpose of securing the stent to the catheter and as a radiation barrier. As shown by an arrow 715, radiation can be directed at distal end 700. A side 720 of sheath 710 can be adapted as described above to increase or decrease the delivered radiation to stent 705. A side 725 can also be adapted to increase the delivered dose to stent 705 through reflection of radiation. Sheath 710 has a thickness Ts that can be adjusted to provide a desired degree of modification of radiation directed at the stent. Ts can be such that the stent receives a delivered radiation that is within a desired or optimal range.

Additionally, a material can be selected having a density that provides the desired degree of modification. The thickness, density, and material can be selected so that the radiation delivered to the stent is increased or decreased to a selected range. In another embodiment, sheath 710 can be disposed over a portion of the catheter to modify the radiation delivered to the portion.

Figure 7C:
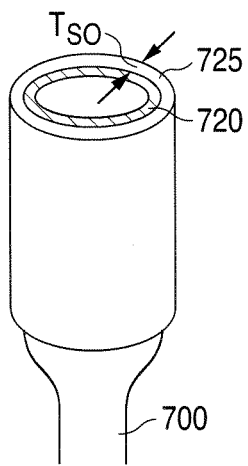
FIG. 7C depicts an inner sheath 720 and an outer sheath 725 over a stent.

FIG. 7C depicts an alternative embodiment of a barrier showing an inner sheath 720 and an outer sheath 725. Inner sheath 720 and outer sheath 725 can act together to modify the delivered radiation to the stent. Inner sheath 720 can be a sheath that is typically used to secure a stent to a catheter, while outer sheath 725 can be designed to adjust the delivered radiation to the stent. For example, a thickness Tso of outer sheath 725 can be adjusted and the density of sheath material can be selected to provide a desired modification of radiation. Various combinations of materials and thicknesses of inner and outer sheaths 720 and 725 can be used to provide an optimal delivered radiation to the stent.

Figure 7D:
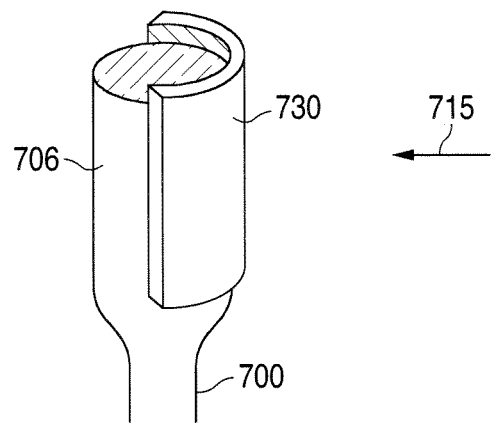
FIG. 7D depicts an embodiment of a covering over a stent. The covering is in the form of a half-cylinder.

FIG. 7D depicts another embodiment of a covering 730 that is in the form of a half-cylinder. Covering 730 covers a side of a selected section 706 of distal end 700 of a catheter 700. Covering 730, for example, can be a reflective material such as metal.

Embodiments of modifier section(s) of the package can selectively modify the radiation from a radiation source so that radiation delivered to a selected section, such as a stent, of a stent delivery assembly is within a selected range. In some embodiments, the modifier sections can have radiation absorption and reflection properties different from other portions of the package. In such embodiments, the modifier section(s) can have a different thickness, density, or be made of a different material. In one embodiment, the modifier section can be coupled to or attached to a package that otherwise has a uniform or substantially uniform thickness, material, and density. For example, the modifier section can be a piece metal, foam, plastic, or other material that is taped, glued, stapled, or attached to the package. In exemplary embodiments, a modifier section can be included in, on, or integral to a pouch 200 shown in FIG. 3 or a box 240 shown in FIG. 4A.

In some embodiments, a package can have a modifier section that is positioned on a side of the selected section facing incoming radiation. The modifier section can then modify radiation through absorption. Additionally or alternatively, a package can have a modifier section that is positioned on a side of the selected section opposite to the incoming radiation. Such a modifier section can modify radiation through reflection or backscattering of radiation at the selected section. The thickness and density of the modifier sections can be selected to obtain a selected delivered radiation to the selected section.

FIG. 8A depicts a schematic illustration of a flexible package 800 with a stent delivery assembly 805 contained therein. A barrier element 810 is attached to a section of package 800. A stent 815 of assembly 805 is positioned behind barrier element 810. FIG. 8B depicts a side view of package 800 showing barrier element 810. FIG. 8B illustrates that package 800 can optionally have a barrier element 820 on its opposite side. In an exemplary embodiment, barrier element 810 can selectively modify radiation directed at assembly 800 from a radiation source, as shown by arrows 825. Additionally, barrier element 820 can modify backscattered radiation as shown by arrows 830 which is reflected, for example, by a supporting fixture (not shown). Barrier element 830 can be reflective material that increases the radiation delivered to the selected section through reflection of radiation that passes through barrier 810. In an alternative embodiment, package 800 can have barrier element 820 and be without barrier element 810.

Barrier elements 810 and 820 can be the same or different thickness, density, or material. In addition, package 800 can optionally include barrier elements 835, 845, or both to modify delivered radiation to a section of the catheter or dispenser coil. The thickness, density, or material of barrier elements 810, 820, 835, and 845 can be selected or adjusted, as discussed in reference to FIGS. 6B-D, to obtain a desired or optimal delivered radiation exposure to stent 815 and selected section 840. In an alternative embodiment, barrier elements can be attached to an inner surface of package 800.

FIGS. 9A-B depicts a schematic illustration of a rigid package or box 900, such as a box 230 shown in FIG. 4, with a stent delivery assembly 905 contained therein. Radiation is directed at package 900 as shown by arrows 925. Backscattered radiation as shown by arrows 930 can come, for example, from a fixture. As shown, assembly 905 is enclosed within a flexible package or pouch 903 which is contained within package 900.

FIG. 9A shows a front view of package 900 with barrier elements 910 and 935 attached to package 900. Barrier element 910 is in front of a stent 915 and barrier element 935 is in front of a section 940 of catheter 905. FIG. 9B shows a side view of package 900. FIG. 9B shows that package 900 optionally includes barrier elements 920, 945, or both on an opposite side of package 900. In an alternative embodiment, package 900 can have either or both barrier elements 920 or 945 and be without barrier elements 910 and 935. The thickness, density, or material of barrier elements 910, 920, 935, and 945 can be selected or adjusted, as discussed in reference to FIGS. 6B-D, to obtain a desired or optimal delivered radiation exposure to stent 915 and section 940.

Figures 10A, 10B:
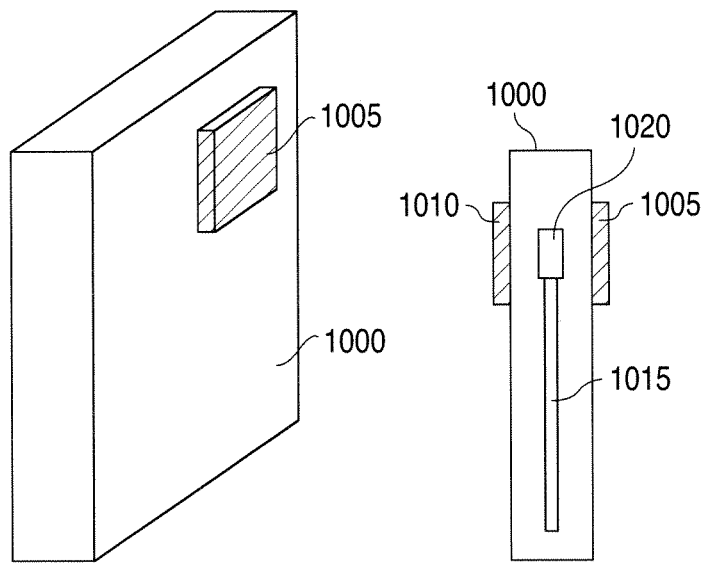
FIG. 10A depicts a package with a preformed barrier portion with a stent delivery assembly contained therein.
FIG. 10B depicts a side view of the package of FIG. 10A.

In further embodiments, the modifier sections of a package can be integral with or incorporated with the packaging. FIG. 10A depicts a package 1000 with a stent delivery assembly (not shown) contained therein. Package 1000 includes a barrier portion 1005 that is integral with, preformed, or incorporated with package 1000. FIG. 10B depicts a side view of package 1000 showing a stent delivery assembly 1015 contained within package 1000. Package 1000 can optionally have a barrier portion 1010. In an alternative embodiment, package 1000 can have barrier element 1010 and be without barrier element 1005. Stent 1020 is positioned between barrier portion 1005 and a barrier portion 1010, which can also be integral with, preformed, or incorporated with package 1000. Package 1000 can be formed of a plastic material with barrier portions 1005 and 1010 preformed as part of package 1000.

Figures 11A, 11B:
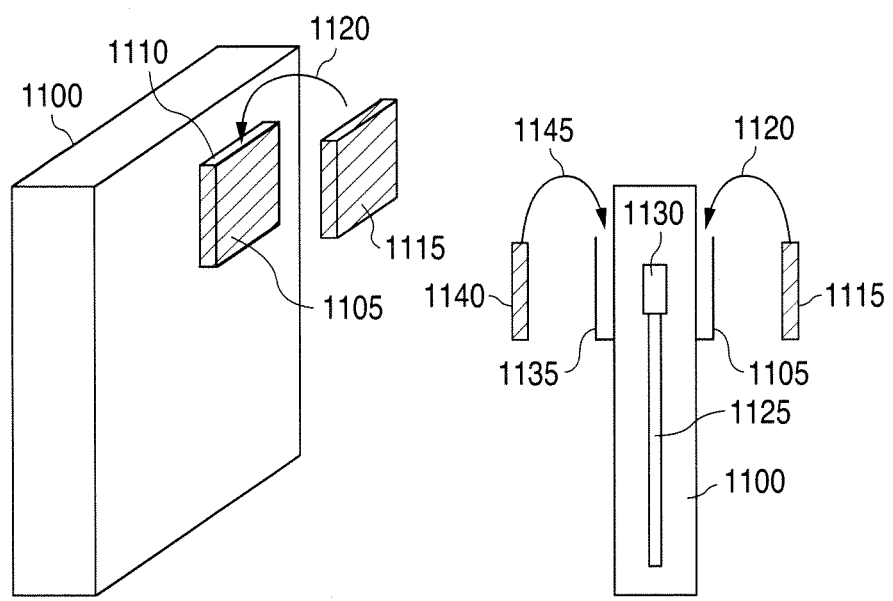
FIG. 11A depicts a package that includes a receptacle or slot for insertion of a barrier element.
FIG. 11B depicts a side view of the package of FIG. 10A.

In additional embodiments, a package can have a receptacle or sleeve that allows insertion of a barrier element. An inserted barrier element can selectively modify radiation delivered to a selected section of a stent delivery assembly. FIG. 11A depicts a package 1100 with a stent delivery assembly (not shown) contained therein. Package 1100 includes a receptacle or slot 1105 that is integral with or attached to package 1100. Receptacle 1105 has an opening 1110 that allows insertion of a barrier element 1115 as shown by an arrow 1120. FIG. 11B depicts a side view of package 1100 showing a stent delivery assembly 1125 contained within package 1100. Package 1100 can also have a receptacle 1135 for a barrier element 1140, as shown by an arrow 1145. In an alternative embodiment, package 1100 can have receptacle 1135 with barrier element 1140 and be without receptacle 1105 with barrier element 1115. Stent 1130 is positioned between receptacle 1105 and a receptacle 1135, which can also be integral with or attached to package 1100.

Further embodiments of the present invention can include sterilizing an implantable medical device using a fixture that selectively modifies the radiation delivered to a selected section of the assembly. In such embodiments, the fixture can be a support arm on a side opposite to the device that faces directed radiation. In an embodiment, the support can include a modifier section that selectively reflects or backscatters radiation to the selected section. For instance, the modifier section can be composed of a material that is more reflective than other portions of the support arm. In another embodiment, the modifier section can selectively absorb radiation or have lower reflective properties than other portions of a support arm.

FIG. 12A depicts a fixture 1200 for supporting packages containing stent delivery assemblies during sterilization. Fixture 1200 includes a bottom support 1205 and a back support 1210. Back support 1210 has a modifier element 1215. Modifier element 1215 has different radiation absorption/reflective properties than other portions of the fixture.

FIG. 12B depicts a side view of fixture 1200 supporting a package 1220 containing a stent delivery assembly 1225. Radiation is directed at package 1220 as shown by an arrow 1235. Stent 1230 is positioned between modifier element 1215 and directed radiation 1235. If back support 1215 is composed of a reflective material, a non-reflective modifier element 1215 can reduce or eliminate backscatter from back support 1210 to stent 1230, reducing delivered radiation to stent 1230. For example, back support 1215 can be composed of aluminum and modifier element 1215 can be a non-reflective material such as foam.

Further embodiments of the present invention can include sterilizing a plurality of stent delivery assemblies disposed on a fixture. A plurality of packages containing assemblies can be positioned on a fixture. The assemblies can be arranged in a planar configuration, such as in box 240 in FIG. 4A. An e-beam from an e-beam source can be at an acute angle to the planar configuration of the packages which are positioned between the radiation source and the fixture. The packages are arranged in a horizontally stacked configuration such that the radiation passes through more than one of the assemblies during exposure. As a result, the delivered dose to the assemblies varies with distance between the radiation source and the fixture. In such embodiments, one or more of the assemblies can be positioned within the packages so that a selected section of the assemblies receives a selected delivered radiation dose.

FIG. 13A depicts a fixture 1300 containing packages 1305 which are arranged in a staggered horizontally stacked configuration. Only three packages are shown, however, it should be understood that the method described applies to more than three. The number of packages is limited by the size of the fixture. Fixture 1300 has a bottom support 1302 and a back support 1304. Each of packages 1305 contain a stent delivery assembly 1310 with a stent 1315 disposed at the distal end of a catheter. FIG. 13B depicts an overhead view of fixture 1300 and packages 1305 along line A-A. A radiation source directs a radiation beam as shown by an arrow 1320. Radiation beam 1320 is at an acute angle θ to the face of packages 1305. The delivered radiation to assembly 1310 in each of packages 1305 decreases with distance along a line parallel to the face of packages 1305, as illustrated by an arrow 1335. A selected section of assembly 1310, such as stent 1315, can be positioned within one or more of packages 1305 so that the selected section has a selected delivered radiation. The delivered radiation to assembly 1310 or a selected section can be increased by a suitable selection of the material of back support 1304. If back support 1304 is composed of a reflective material, the delivered radiation to assembly 1310 or a selected section can be increased. Alternatively, if back support 1304 is composed of a non-reflective material, such as foam, increase of delivered radiation due to reflected radiation can be reduced or prevented. Additionally, a modifier section 1215 as depicted in FIGS. 12A-B can be used with fixture 1300 to selectively modify delivered radiation to a selected section.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

A polymer for use in fabricating an implantable medical device, such as a stent, can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed and/or eliminated by the body. The processes of breaking down and absorption of the polymer can be caused by, for example, hydrolysis and metabolic processes.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate a substrate of an implantable medical device or a coating for an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

A non-polymer substrate of the device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

A drug or active agent can include, but is not limited to, any substance capable of exerting a therapeutic, prophylactic, or diagnostic effect. The drugs for use in the implantable medical device, such as a stent or non-load bearing scaffolding structure may be of any or a combination of a therapeutic, prophylactic, or diagnostic agent. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin.

A stent storage container, for example, package 230 of FIG. 3 or package 1100 of FIGS. 11A-B, can be made of various substances that form a barrier when sealed. For instance, at stent storage container can be made of a polymer, glass, ceramic or a metallic substance such as aluminum, stainless steel or gold. If made of a metallic substance, the container for example can be formed of a metallic film. Suitable examples of films include, but are not limited to, gold, platinum, platinum/iridium alloy, tantalum, palladium, chromium, and aluminum. Suitable materials for the container may also include oxides of the above-mentioned metals, for example, aluminum oxide. Medical storage containers may be obtained from, for example, Oliver Products Company of Grand Rapids, Mich.

Suitable polymers for construction of a stent storage container can include polymers of polyolefins, polyurethanes, cellulosics (i.e., polymers having mer units derived from cellulose), polyesters, polyamides, poly(hexamethylene isophthalamide/terephthalamide) (commercially available as Selar PA™), poly(ethylene terephthalate-co-p-oxybenzoate) (PET/PHB, e.g., copolymer having about 60-80 mole percent PHB), poly(hydroxy amide ethers), polyacrylates, polyacrylonitrile, acrylonitrile/styrene copolymer (commercially available as Lopac™), rubber-modified acrylonitrile/acrylate copolymer (commercially available as Barex™), liquid crystal polymers (LCP) (e.g. Vectra™ available from Hoescht-Celanese, Zenite™ available from DuPont, and Xydar™ available from Amoco Performance Chemicals), poly(phenylene sulfide), polystyrenes, polypropylenes, polycarbonates, epoxies composed of bisphenol A based diepoxides with amine cure, aliphatic polyketones (e.g., Carilon™ available from Shell, and Ketonex™ available from British Petroleum), polysulfones, poly(estersulfone), poly(urethane-sulfone), poly(carbonate-sulfone), poly(3-hydroxyoxetane), poly(amino ethers), gelatin, amylose, parylene-C, parylene-D, and parylene-N.

Representative polyolefins include those based upon alpha-monoolefin monomers having from about 2 to 6 carbon atoms and halogen substituted olefins, i.e., halogenated polyolefins. By way of example, and not limitation, low to high density polyethylenes, essentially unplasticized poly(vinyl chloride), poly(vinylidene chloride) (Saran™), poly(vinyl fluoride), poly(vinylidene fluoride), poly(tetrafluoroethylene) (Teflon), poly(chlorotrifluoroethylene) (Kel-F™), and mixtures thereof are suitable. Low to high density polyethylenes are generally understood to have densities of about 0.92 g cm$^{-3}$ to about 0.96 g cm$^{-3}$, however, no bright line can be drawn for density classifications and the density can vary according to the supplier.

Representative polyurethanes include polyurethanes having a glass transition temperature above a storage or ambient temperature, for example having a glass transition temperature of at least 40° C. to 60° C., or having a non-polar soft segment which includes a hydrocarbon, silicone, fluorosilicone, or mixtures thereof. For example, Elast-Eon™ manufactured by Elastomedic/CSIRO Molecular Science, is a polyurethane with a non-polar soft segment which is made from 1,4-butanediol, 4,4'-methylenediphenyl diisocyanate, and a soft segment composed of a blend of poly(hexamethylene oxide) (PHMO) and bishydroxyethoxypropylpolydimethylsiloxane (PDMS). A useful example has a blend of 20% by weight PHMO and 80% by weight PDMS.

Representative examples of cellulosics include, but are not limited to, cellulose acetate having a degree of substitution (DS) greater than about 0.8 or less than about 0.6, ethyl cellulose, cellulose nitrate, cellulose acetate butyrate, methyl cellulose, and mixtures thereof.

Representative polyesters include saturated or unsaturated polyesters such as, but not limited to, polybutylene terephthalate), poly(ethylene 2,6-naphthalene dicarboxylate) (PEN), and poly(ethylene terephthalate).

Representative polyamides include crystalline or amorphous polyamides such as, but not limited to, nylon-6, nylon-6,6, nylon-6,9, nylon-6,10, nylon-11, aromatic nylon MXD6 (manufactured by Mitsubishi Gas Chemical America, Inc.), and mixtures thereof.

Representative polyacrylates include, but are not limited to, poly(methylmethacrylate) and polymethacrylate.

A stent storage container may also be composed of copolymers of vinyl monomers with each other and olefins such as poly(ethyl vinyl acetate).

While particular embodiments of the present invention have been shown and described, it will be obvious to those skilled in the art that changes and modifications can be made without departing from this invention in its broader aspects.

What is claimed is:

1. A system for radiation sterilization, comprising:
a stent delivery assembly; and
a package having one or more modifier sections, the stent delivery assembly being disposed within the package, wherein the one or more modifier sections are positioned relative to a selected section of the stent delivery assembly to modify radiation delivered to the selected section of the assembly when the radiation is directed at the stent delivery assembly from a radiation source.

2. The system of claim 1, wherein a first modifier section is positioned behind the selected section and a second modifier section is positioned in front of the selected section, wherein the first and second modifier sections are configured to modify the radiation delivered to the selected section from the radiation source by the radiation passing through the first modifier section and through backscattering of the radiation from the second modifier section.

3. The system of claim 1, wherein a first modifier section is positioned behind the selected section, wherein the first modifier section is configured to modify the radiation delivered to the selected section from the radiation source through backscattering of the radiation.

4. The system of claim 1, wherein a first modifier section is positioned in front of the selected section, wherein when the first modifier section receives a delivered radiation dose from the radiation source the selected section receives a modified radiation dose, the modified radiation dose being less than the delivered radiation dose and within an optimal range for sterilizing the selected section.

5. The system of claim 1, wherein a first modifier section increases or decreases the radiation delivered to the selected section from the radiation source.

6. The system of claim 1, wherein the selected section comprises a polymeric stent.

7. The system of claim 1, wherein the package is a sealed package.

8. The system of claim 1, wherein the package is a pouch, container or box.

9. The system of claim 8, wherein the pouch is made of metallic foil.

10. The system of claim 1, wherein the one or more modifier sections are glued, stapled or taped to the package.

11. The system of claim 1, wherein the one or more modifier sections are inside the package.

12. The system of claim 1, wherein the one or more modifier sections are integral with the package.

13. The system of claim 1, wherein the stent delivery assembly is sealed in the package and the stent delivery assembly is transported in the package after sterilization of the stent delivery assembly.

14. The system of claim 1, wherein a first modifier section includes a barrier element for reflecting the radiation.

15. The system of claim 1, wherein the one or more modifier sections are attached to the package.

16. The system of claim 1 wherein the package includes a sleeve or receptacle that receives a first modifier section.

17. The system of claim 1, wherein a first modifier section has a thickness selected according to a dose-distribution curve, such that a delivered dose is reduced to a modified dose at the selected section, the modified dose being within an optimal range for sterilization of the selected section.

* * * * *